United States Patent [19]

Herzog et al.

[11] Patent Number: 4,983,728

[45] Date of Patent: Jan. 8, 1991

[54] NUCLEIC ACID PROBES OF HUMAN PAPILLOMA VIRUS

[75] Inventors: Albert Herzog, Eppegem; Alfredo Cravador, Rhode-St-Genese; Sophie Houard, Brussels; Alex Bollen, Itterbeek, all of Belgium

[73] Assignee: Ire-Celltarg S.A., Fleurus, Belgium

[21] Appl. No.: 225,381

[22] Filed: Jul. 28, 1988

[30] Foreign Application Priority Data

Jul. 31, 1987 [FR] France ............................ 87 10917
Apr. 5, 1988 [FR] France ............................ 88 04436

[51] Int. Cl.$^5$ ..................... C12Q 1/68; C07H 21/04; G01N 33/571; C12P 19/34
[52] U.S. Cl. ............................... 536/27; 435/6; 435/91; 435/948; 436/501; 436/811; 935/9; 935/16; 935/17; 935/78; 935/88
[58] Field of Search ............... 435/6, 91, 948; 436/501, 811; 536/27; 935/9, 16, 17, 78, 88

[56] References Cited

FOREIGN PATENT DOCUMENTS 0133123 2/1985 European Pat. Off. .
0192001 8/1986 European Pat. Off. .
0235004 9/1987 European Pat. Off. .
0243221 10/1987 European Pat. Off. .
8303623 10/1983 World Int. Prop. O. .
8605816 10/1986 World Int. Prop. O. .

OTHER PUBLICATIONS

Danos et al. (1982), EMBO Journal Vol. 1, No. 2, pp. 231–236.
Schwarz et al. (1983), EMBO Journal vol. 2, No. 12, pp. 2341–2348.
Saiki et al. (1985), Science, vol. 230, pp. 1350–1354.
Chemical Abstracts, vol. 107, 1987, p. 409, #232380e, Columbus, Ohio, U.S., S. Syrjanen et al.: "Comparison of In Situ DNA Hybridization Protocols Using Sulfur-35-Labeled and Biotin-Labeled Probes in Detection of Human Papillomavirus DNA Sequences" & Cancel Cells 1987, 5 (Papillomaviruses), 329–36.
Chemical Abstracts, vol. 104, 4/86, p. 340, resume #125877p, Columbus, Ohio, U.S., by J. K. McDougall et al.: "Detection of Viral DNA and RNA by In Situ Hybridization", and J. Histochem. Cytochem. 1986, 34(1), 33–8.
Chemical Abstracts, vol. 105, 1986, p. 527, No. 169878q, Columbus, Ohio, U.S., K. Milde et al.: "Detection of Papillomavirus DNA in Oral Papillomas and Carcinomas: Application of In Situ Hybridization with Biotinylated HPV 16 Probes" & J. Oral Pathol. 1986, 15(5), 292–6.

Primary Examiner—Amelia Burgess Yarbrough
Assistant Examiner—Ardin Marschel
Attorney, Agent, or Firm—Fleit, Jacobson, Cohn, Price, Holman & Stern

[57] ABSTRACT

The present invention relates to probes of nucleic acids useful for detecting indifferently the various types of human papilloma virus, particularly HPV1a, HPV5, HPV6b, HPV8, HPV11, HPV16, HPV18 and HPV33, especially a probe comprising a labelled sequence of nucleic acids, characterized in that it comprises the oligomer of twelve nucleotides X-A-A-A-A-C-G-A-A-A-G-X, with X=T or U, or its complement by interchanging A and X on the one hand, C and G on the other hand. The present invention also relates to specific probes of nucleic acids for the detection of human papilloma for each of the types HPV1a, HPV5, HPV8, HPV11, HPV16, HPV18 and HPV33, as well as specific probes of sub-groups of the virus HPV16, HPV18, HPV33 or HPV16 and HPV18 only or again HPV5 and HPV8 only.

17 Claims, 5 Drawing Sheets

NUCLEIC ACID PROBES OF HUMAN PAPILLOMA VIRUS

BACKGROUND OF THE INVENTION

The technical field of the present invention is that of probes constituted by labelled, mono-strand DNA or RNA nucleic acid sequences.

Such probes are well known in the state of the art and may be obtained by various routes particularly by genetic engineering or by manual or automatic direct synthesis.

These nucleic acid sequences have the property of being matched and of forming hybrids with complementary DNA sequences, as the case may be, denaturated previously, if the latter were initially bicatenary or mRNA. This denaturation can be done after incubation in a medium of high ionic strength and at high temperature or in a basic medium. These hybrids are then detectable.

The detection of the hybrids can be done by different methods. The probe may be labelled by one of the known methods for the labelling of nucleic acid probes. It may be radioactive labelling, for example with phosphorus 32, or in the case of a cold probe, non-radioactive labelling, for example enzymatic, as is also known. In certain cases, the probe is not labelled during its use proper, but modified chemically to be detectable after hybridization, for example with biotin.

More precisely, the present invention relates to nucleic acid probes enabling the detection of different types of human papilloma virus by hybridization with the DNA of the virus. It relates particularly to eight types of human papilloma virus (HPB) of which all the DNA sequences are known today, namely the types HPV1a, HPV5, HPV6b, HPV8, HPV11, HPV16, HPV18 and HPV33.

10% of women are infected with the HPV virus; the virus is located in the cervical cells and leads in a certain number of cases to dysplasic and/or malignant lesions of the cervix, Among the various types of HPV virus, HPV16 and HPV18 seem most frequently associated with these lesions.

HPVs are characterized by a circular double strand DNA genome, about 8000 pairs of bases long, wrapped in a protein capsid 60 nm in diameter. The virus subsists in non-malignant lesions in the unintegrated episome state. In these cases disturbance of the cellular differentiation is observed and the production of viral particles at late stages of the differentiation. When uterine carcinoma is established, a variable integration of certain sequences of viral DNA in the cellular DNA is observed.

The detection of HPV virus in the cervix is carried out by the use of molecular probes constituted by isotopically cloned and labelled viral DNA fragments.

Within the framework of epidemiological studies and routine diagnosis of infections by HPV, it is useful to develop a rapid simple specific and sensitive method based on the use of synthetic DNA probes labelled non-isotopically and usable in situ. To this end, there are identified, at the level of the DNA, specific regions of different types of HPV virus to deduce therefrom complementary homologous synthetic probes. The nucleotide sequences of HPV1, HPV5, HPV6, HPV11, HPV16, HPV18 and HPV33 are known.

It is an object of the present invention to provide probes characteristic of all the various types of HPV virus particularly mentioned above which are effective, that is to say probes having the longest possible nucleic acid sequences and which are common to the various types of HPV virus.

Another object of the present invention is also to provide specific probes for each of the various types of HPV virus and which ensure stable matching.

GENERAL DESCRIPTION OF THE INVENTION

It is accordingly an object of the present invention to provide a nucleic acid probe useful for detecting indifferently the various types of human papilloma virus, particularly HPV1a, HPV5, HPV6b, HPV8, HPV11, HPV16, HPV18 and HPV33, characterized in that it comprises the oligomer:

X-A-A-A-A-C-G-A-A-A-G-X or its complement by interchanging A and X on the one hand, C and G on the other hand, in the case where the target DNA of the virus was initially bicatenary and has been denaturated before being probed, with X=T or U or in the case where the mRNA is probed.

A,T,G,C,U represent nucleotides corresponding to the bases adenine, thymine, cytosine, guanine and uracil respectively.

The sequence T-A-A-A-A-C-G-A-A-A-G-T is the only one which is again found in fact, particularly in the DNA of each of the eight types of HPV virus among the sequences at least 10 bases long.

This sequence corresponds to the sequences situated on the strand coding the following positions of the first nucleotide in the various types of virus:

for HPV1a: position 1029
for HPV5: position 1190
for HPV6b: position 1076
for HPV8: position 1174
for HPV11: position 1076
for HPV16: position 1121
for HPV18: position 1167
for HPV33: position 1132

It is also an object of the present invention to provide a nucleic acid probe common to the different types of HPV virus, characterized in that it comprises the mixture of 6 oligomers each comprising the common sequence of 12 nucleotides previously targeted, extended upstream and downstream by nucleotides corresponding to the eight types of HPV virus. These extensions are constituted by nucleotides matching the nucleotides immediately surrounding the sequence common to the eight types of HPV virus T-A-A-A-A-C-G-A-A-A-G-T. Among these oligomers, four are associated each with a different type of virus, the fifth is common to the viruses 6b and 11, another is common to the viruses 5 and 8.

For example, it is possible to prolong the common sequence of 12 nucleotides on each side of 1 to 10 of the corresponding nucleotides for each virus type.

By prolonging up to 6 or 7 nucleotides on each side of the common sequence, the 6 following oligomers or their complements are obtained:

for HPV1a   A-X-G-C-X-X-X-A-A-A-A-C-G-A-A-A-G-X-X-A-C-X-X-X

| | |
|---|---|
| for HPV6b and HPV11 | A-G-G-A-C-C-X-A-A-A-A-C-G-A-A-A-G-X-A-X-X-X-A-G |
| for HPV8 and HPV5 | C-A-A-A-A-A-C-X-A-A-A-A-C-G-A-A-A-G-X-A-X-C-X-X-A |
| for HPV16 | A-G-G-X-X-C-X-A-A-A-A-C-G-A-A-A-G-X-A-X-X-X-G-G |
| for HPV18 | A-X-G-X-X-X-X-A-A-A-A-C-G-A-A-A-G-X-X-X-G-C-A-G |
| for HPV33 | G-X-G-C-A-C-X-A-A-A-A-C-G-A-A-A-G-X-X-X-G-C-C-G |

These oligomers correspond to DNA target sequences of the viruses at the following positions for each type of HPV virus:
for HPV1a: position 1023
for HPV5: position 1183
for HPV6b: position 1070
for HPV8: position 1167
for HPV11: position 1070
for HPV16: position 1115
for HPV18: position 1161
for HPV33: position 1126

An extension of four bases on each side of the common sequence only provides sequences giving half-hybridization temperatures of the order of 50° to 52° C. On the other hand, from six bases, both upstream and downstream, corresponding therefore to the exact sequences present in the viruses, half-hybridization temperatures of the order of 60° to 70° C. are obtained.

Thus for the target sequence of HPV1a (in position 1023) the probe has a predictable half-hybridization temperature of 60° C.,
for HPV5 (position 1183) T=62° C.
for HPV6b (position 1070) T=64° C.
for HPV8 (position 1167) T=62° C.
for HPV11 (position 1070) T=64° C.
for HPV16 (position 1115) T=64° C.
for HPv18 (position 1161) T=62° C.
for HPV33 (position 1126) T=70° C.

These oligonucleotide probes common to all known human papilloma viruses permit rapid diagnosis of disorders based on a papilloma virus.

It is another object of the present invention to provide a series of eight nucleic acid probes each specific to one type of human papilloma virus with respect to the other types, namely the following oligomers or their complements:
for HPV1a: l'oligomer C-C-X-C-A-G-G-C-G-A-G-A-A-G-C-G-C-G-G-A-C
for HPV5: l'oligomer X-G-X-A-X-G-G-G-A-X-C-G-G-G-G-C-G-X-X-X-A
for HPV6b: l'oligomer C-A-X-X-A-A-C-G-C-A-G-G-G-G-C-G-C-C-X-G-A-A
for HPV8: l'oligomer A-C-A-C-C-G-C-C-G-C-C-A-A-G-A-C-C-C-C-A
for HPV11: l'oligomer G-G-C-G-X-G-X-C-G-G-C-G-C-C-G-C-C-X-A-G
for HPV16: l'oligomer C-A-G-A-A-C-G-G-A-C-A-G-A-G-C-C-C-A-X
for HPV18: l'oligomer C-G-G-X-A-X-C-C-G-C-X-A-C-X-C-A-G-C-X-X-G
for HPV33: l'oligomer C-G-X-C-C-X-C-C-G-G-X-X-A-C-X-G-X-A-G-A-C-A with X=T or U.

It is possible to contemplate the use of the complementary oligomers when the DNA to be probed was initially bicatenary and has been denaturated to be hybridable or in the case where mRNA is probed.

The selective oligomer for HPV1a comprises 21 monomers, and this sequence corresponds to the 1052 position of the DNA of the virus and has a half-hybridization temperature of 72° C.

The selective oligomer for HPV5 comprises 22 monomers, this sequence corresponding to the 1801 position of the DNA of the virus and has a half-hybridization temperature of 68° C.

The selective oligomer for HPV6b comprises 22 monomers, this sequence corresponds to the 4761 position of the DNA of the virus and has a half-hybridization temperature of 70° C.

The selective oligomer for HPV8 comprises 21 monomers, this sequence corresponds to the 3344 position of the DNA of the virus and has a half-hybridization temperature of 72° C.

The selective oligomer for HPV11 comprises 20 monomers, this sequence corresponds to the position 3416 of the DNA of the virus and has a half-hybridization temperature of 72° C.

The selective oligomer for HPV16 comprises 20 monomers, this sequence corresponds to the position 695 of the DNA of the virus and has a half-hybridization temperature of 64° C.

The selective oligomer for HPV18 comprises 21 monomers, this sequence corresponds to the position 3448 of the DNA of the virus and has a half-hybridization temperature of 64° C.

The selective oligomer for HPV33 comprises 22 monomers, this sequence corresponds to the position 4474 of the DNA of the virus and has a half-hybridization temperature of 68° C.

The finality of this second series of specific probes of one or other of the eight human papilloma viruses is to be used as selective elements for diagnostic tests of infections by these viruses.

It is also an object of the present invention to provide a second series of eight single strand DNA or RNA nucleic acid probes, each specific to one type of human papilloma virus with respect to the other types. They are alternate selective probes with respect to those previously described.

These probes comprise a labelled nucleic acid sequence including the following oligomers:

| | |
|---|---|
| for HPV1a | CXGXCCCXXCXGCGCGAGACGX |
| for HPV5 | XXGXAXGGGAXCGGGGGCGXXXA |
| for HPV6b | GGCAAXCAXXAACGCAGGGGCG |
| for HPV8 | GCAGCXCAGXCCGCGGCXCC |
| for HPV11 | GAAGCXCXCCCAAGCCXGCXAXX |
| for HPV16 and | ACCAGAGACAACXGAXCXCXACXG ACAAGCAGAACCGGACAGAGCCCA |
| for HPV18 | CCCAXXGXAXCACCCACGGCCC |
| for HPV33 | GXCCXCCGGXXACXGXAGACACX |

The above sequences correspond to the sequences of the direct or coding string or strand of the DNA of the virus and can be hybridized with the bicatenary DNA or with the reverse string when the DNA has been denatured.

It is also possible, of course, to use complementary oligomers by interchanging A and X on the one hand, and C and G on the other hand. These complementary oligomers are particularly useful as probes to be hybridized with the messenger RNA of the virus.

It is recalled that in the above sequences, A,T,C,G and U represent nucleotides corresponding to the bases adenine, thymine, cytosine, guanine and uracil respectively, and X represents T or U.

The selective oligomer for HPV1a comprises 22 monomers. The first nucleotide of this sequence corresponds to the 3448 position of the strand coding the DNA of the virus. The sequence ends at position 3469. This sequence corresponds to a position situated in the E3 gene of the HPV1a virus and has a half-hybridization temperature of 72° C.

The selective oligomer for HPV5 comprises 23 monomers. This position corresponds to the position 1800-1822 of the DNA of the virus situated in the E1 gene and has a half-hybridization temperature of 70° C.

The selective oligomer for HPV6b comprises 22 monomers. This position corresponds to the position 4755-4776 of the DNA of the virus situated in the L2 gene and has a half-hybridization temperature of 70° C.

The selective oligomer for HPV8 comprises 20 monomers. This position corresponds to the position 1208-1227 of the DNA of the virus situated in the E1 gene and has a half-hybridization temperature of 70° C.

The selective oligomer for HPV11 comprises 23 monomers. This position corresponds to the position 4637-4659 of the DNA of the virus situated in the L2 gene and has a half-hybridization temperature of 70° C.

The first selective oligomer for HPV16 comprises 24 monomers. This sequence corresponds to the position 609-632 of the DNA of the virus situated in the E7 gene and has a half-hybridization temperature of 70° C.

For the virus HPV16 a second specific probe of 24 monomers was determined, it is situated in the E7 gene devoid of any T or U bases, it is located at position 690-713.

The selective oligomer for HPV18 comprises 22 monomers. This sequence corresponds to the position 5486-5507 of the DNA of the virus situated in the L2 gene and has a half-hybridization temperature of 72 C.

The selective oligomer for HPV33 comprises 23 monomers. This sequence corresponds to the position 4475-4497 of the DNA of the virus situated in the L2 gene and has a half-hybridization temperature of 70° C.

the virus. It is therefore also an object of the invention to provide complementary sequences which can be hybridized particularly with the messenger RNA of the virus.

These novel specific probes consist of labelled nucleic acid sequences, comprising the following oligomers:

For HPV1a: XGXCCCXXCXGCGCGAGACGX-XGGAAGXAXACACA.

This sequence corresponds to the position 3449-3482 of the strand coding the DNA of the virus and is situated in the E3 gene.

For: HPV5: XGXAXGGGAXCGGGGGCGXXX-AGCCAXGGACCAXA.

This sequence corresponds to the position 1801-1835 of the DNA of the virus, it is situated in the E1 gene.

For: HPV6b: GCAAXCAXXAACG-CAGGGGCGCCXGAAAXXGXGCC.

This sequence corresponds to the position 4756-4790 of the DNA of the virus and is situated in the L2 gene.

For: HPV8: GCAGCXCAGXCCGCGGCXCCAGX-CAAXAXCACXGX.

This sequence corresponds to the position 1208-1242 of the DNA of the virus and is situated in the E1 gene.

For: HPV11: XAXAXACCCXXGGGAAGCXCX-CCCAAGCCXGCXAX.

This sequence corresponds to the position 4624-4658 of the DNA of the virus and is situated in the L2 gene.

For: HPV16: XGXXAGAXXXGCAAC-CAGAGACAACXGAXCXCXAC.

This sequence corresponds to the position 596-630 of the DNA of the virus and is situated in the E7 gene.

For: HPV18: CCCAXXGXAXCACC-CACGGCCCCXGCCXCXACACA.

This sequence corresponds to the position 5486-5520 of the DNA of the virus and is situated in the L2 gene.

This sequence corresponds to the position 4476-4510 of the DNA of the virus and is situated in the L2 gene.

It is also an object of the present invention to provide other nucleic acid probes each specific to types of human papilloma virus but always situated in the E7 region of the genome of each of these viruses.

In fact, the E7 gene of the genome of each of these HPV viruses is the most concerned in the integrated form of these viruses in the DNA of malignant cells.

This third series of specific probes comprises oligonucleotides of a length such that they have a half-hybridization temperature of 70° C. They are the following oligomers or their complements:

| Virus  | Oligomer                            | Length | Position | Gene |
|--------|-------------------------------------|--------|----------|------|
| HPV1a  | GACCGXCCXCGCGGAXCACAG               | 21     | 711-731  | E7   |
| HPV5   | GCCXGACAACGAAAGGAXCXCXXA            | 24     | 788-811  | E7   |
| HPV6b  | GACGAAGXGGACGGACAAGAXXC             | 23     | 641-663  | E7   |
| HPV8   | XGXCAACGCAACXGAXXCGGGXAX            | 24     | 856-879  | E7   |
| HPV11  | XGAGGXGGACAAGGXGGACAAAC             | 23     | 634-656  | E7   |
| HPV16  | AGXGXGACXCXACGCXXCGGXXG             | 23     | 740-762  | E7   |
| HPV18  | XXGXAAGXGXGAAGCCAGAAXXGAG           | 25     | 784-808  | E7   |
| HPV33  | AGCAAGXGACCXACGAACCAXACA            | 24     | 788-811  | E7   |

It is also an object of the present invention to provide another series of probes each specific to HPV virus types with respect to other virus types. These probes have a length of 35 monomers. They are the preceding specific probes, lengthened upstream or downstream according to the marked zones of analogy. These oligomers correspond also to the strand coding the DNA of It is another object of the present invention to provide a novel series of specific nucleic acid probes of the E7 region of each of the HPV virus types with respect to other virus types, these probes comprising oligonucleotides of 35 monomers length, namely the following oligomers or their complements:

| Virus | Oligomer | Position |
|---|---|---|
| HPV1a | GACCGXCCXCGCGGAXCACAGCGCCAXXAGACAGC | 711-745 |
| HPV5 | GAGGAGCCXGACAACGAAAGGAXCXCXXACAAAGX | 783-817 |
| HPV6b | GAGGXGGACGAAGXGGACGGACAAGAXXCACAACC | 635-669 |
| HPV8 | CXXXXXGXCAACGCAACXGAXXCGGGXAXCAGGAC | 851-885 |
| HPV11 | AGAAGAXGAGGXGGACAAGGXGGACAAACAAGACG | 628-662 |
| HPV16 | XXGCAAGXGXGACXCXACGCXXCGGXXGXGCGXAC | 735-769 |
| HPV18 | AXGXGXXGXAAGXGXGAAGCCAGAAXXGAGCXAGX | 779-813 |
| HPV33 | AGXACAGCAAGXGACCXACGAACCAXACAGCAACX | 783-817 |

These series of probes correspond like the preceding ones to the coding strand of the DNA of the virus and their complements with the reverse strand which can hence be hybridized with the messenger RNA particularly. The indicated positions correspond to the direct strand as for the preceding ones.

The present invention also relates to probes which permit HPV viruses to be distinguished which are responsible for tumors of the skin of those, belonging to the mucus membranes, which cause anogenital cancers or those of the oral, nasal and paranasal tracts.

It is also an object of the present invention to provide specific probes of the virus sub-group constituted by HPV16, HPV18 and HPV33 which cause tumors of the mucus membranes, characterized in that they include the following sequence:

XXAGGCACAXAXXXX or its complement.

This sequence is common to HPV16, HPV18 and HPV33 and is not to be found again in other types of HPV virus.

It is situated at the following positions (numbering with respect to the coding string)

| Virus | Position | Gene |
|---|---|---|
| HPV16 | 7698-7712 | downstream of L1 |
| HPV18 | 7686-7700 | downstream of L1 |
| HPV33 | 7741-7755 | downstream of L1 |

It is equally an object of the present invention to provide specific probes of the sub-group HPV16, HPV18 which cause tumors of the mucus membranes, characterized in that they include the following sequence:

AXAXCAAAXAXXAGXGAAGX or its complement

This sequence is common to HPV16 and HPV18 and is not to be found again in any of the other types of HPV virus.

It is situated at the following positions (numbering with respect to the coding string)

| Virus | Position | Gene |
|---|---|---|
| HPV16 | 1840-1859 | E1 |
| HPV18 | 1910-1929 | E1 |

Lastly, it is an object of the present of the present invention to provide a specific probe of the virus sub-group consisting of HPV5 and HPV8 which causes tumors of the skin characterized in that it comprises a fragment 56 bases long whose sequence defined with respect to the coding string is as follows:

CAAACAACAGXXGCXGACAAXAXXXX-
AAAAXAXGGCAGXGCXGGXGXAXXX
XXXGG it is situated at the following positions (numbering with respect to the coding string)

| Virus | Position | Gene |
|---|---|---|
| HPV5 | 4450-4505 | L2 |
| HPV8 | 4383-4438 | L2 |

Within this fragment, it is possible to select shorter sequences having half-hybridization temperatures of the order of 70° C. Among these various possibilities, may be mentioned the probe including the sequence

XAXGGCAGXGCXGGXGXAXXXXXXG or its complement

This sequence corresponds to the positions 4480-4504 of HPV5 and 4413-4437 of HPV8 (numbered with respect to the coding string).

The selected probes, common to each of the HPV virus sub-groups, permits the identification of each of the sub-groups and, through their selectivity, them to be distinguished from one another.

It is also an object of the present invention to provide a nucleic acid probe, characterized in that it is labelled by one of the methods known for the labelling of DNA or RNA probes, selected particularly from among radioactive labelling such as with $^{32}P$ and enzymatic labelling such as with biotin, as well as a method of detection of an HPV virus type or of an HPV virus sub-group by means of a probe, according to the invention, characterized in that said probe is hybridized with a DNA or RNA sequence of said HPV viruses, as the case may be, previously denaturated if it was initially bicatenary.

DESCRIPTION OF THE DRAWINGS

Other advantages and characteristics of the present invention will appear in the light of the following description.

In the accompanying drawings.

1. radioactive DNA fragments lambda EcoRI-HindIII standards of size,
2. DNA of the HPV6b virus, digested with BamHI.
3. DNA of the HPV11 virus, digested with BamHI,
4. DNA of the HPV16 virus, digested with BamHI,
5. DNA of the HPV18 virus, digested with EcoRI,
A. specific probe of HPV6b,
B. specific probe of HPV11,
C. specific probe of HPV16, D. specific probe of HPV18.

DESCRIPTION OF PREFERRED EMBODIMENTS EXAMPLE 1

Determination of oligonucleotide probes common to all the known human papilloma viruses For the preparation of a probe enabling rapid diagnosis of disorders based on the papilloma virus, research has been pursued into the longest sequences which are common to all the viruses whose sequence is known today, namely up till now sequences of the following viruses HPV1a, HPV5, HPV6b, HPV8, HPV11, HPV16, HPV18, and HPV33.

A FORTRAN program was specifically developed for the work concerned, the usual algorithms being unsuitable for manipulation of several such extended sequences. The program explores each of the sequences which are subjected to it by means of all possible blocks extracted from the first among them, these blocks successively taking the values between 20 and 10 bases in length. In the course of this search, the program announces the occurence of blocks integrally preserved through all of the sequences which are submitted to it.

The longest common sequence found, namely the fragment of 12 bases (T-A-A-A-A-C-G-A-A-A-G-T) is situated at the following positions in the various sequences:

| | |
|---|---|
| HPV1a | 1029 |
| HPV5 | 1190 |
| HPV6b | 1076 |
| HPV8 | 1174 |
| HPV11 | 1076 |
| HPV16 | 1121 |
| HPV18 | 1167 |
| HPV33 | 1132 |

As twelve bases constitute too short a fragment to serve easily under certain experimental conditions, this sequence was lengthened upstream and downstream.

An extension of 4 bases on each side only provided sequences giving half-hybridization temperatures of the order of 50°-52° C. Therefore it was extended by 6 or 7 bases both upstream and downstream, each time by exact sequences present in the viruses to give the following:

| Target sequence | | Position | Temperature |
|---|---|---|---|
| HPV1a | ATGCTTTAAAACGAAAGTTACTTT | 1023 | 60° C. |
| HPV5 | CAAAAACTAAAACGAAAGTATCTTA | 1183 | 62° C. |
| HPV6b | AGGACCTAAAACGAAAGTATTTAG | 1070 | 64° C. |
| HPV8 | CAAAAACTAAAACGAAAGTATCTTA | 1167 | 62° C. |
| HPV11 | AGGACCTAAAACGAAAGTATTTAG | 1070 | 64° C. |
| HPV16 | AGGTTCTAAAACGAAAGTATTTGG | 1115 | 64° C. |
| HPV18 | ATGTTTTAAAACGAAAGTTTGCAG | 1161 | 62° C. |
| HPV33 | GTGCACTAAAACGAAAGTTTGCCG | 1126 | 70° C. |

Certain of these probes may be somewhat shortened and that specific of HPV8 can also if necessary be extended to obtain almost identical half-denaturation temperatures.

It is to be noted that the sequences obtained for HPV6b and HPV11 are identical, in the same way for HPV5 and HPV8. The oligonucleotide mixture therefore only includes six different molecules.

The mixing of these six oligonucleotides enables the obtaining, for any system including the DNA of one of the human papilloma viruses, of a quite characteristic hybridization signal.

EXAMPLE 2

Determination of specific probes of each of the known types of HPV (first series of probes)

The work consisted of searching for oligonucleotide probes of a length in the vicinity of 20 bases, and selected so that they are each specific to one or other of the eight human papilloma viruses whose complete sequences are known today. Their finality is to be used as selective elements for diagnostic tests of infections by these viruses.

For this purpose a specific software has been developed, comprising FORTRAN programmes, and intended for the comparison of several large-sized sequences, for the detection of the least preserved regions. This programme operates like a progressive filter, marking at each of its successive executions the regions of a sequence which are found again exactly in each of the other sequences concerned. After each passage, the length of the homology sought is decremented by one unit, between the initial value of 25 and the final value of 8.

Each of the versions of the reference sequence, marked during each of the successive passages with each of the targeted sequences, is stored separately. A second programme then determines between the various marked sequences, the unmarked regions, and this for each of the successive stages of the filtering At the output, a list of the potentially useful regions is obtained. The choice among these regions is effected by an examination of the environment of the region during preceding passages of the filter, so that the oligomer selected shows a minimum of homology with the DNA sequences of the other viruses.

Thus, for example, the first series of the following oligomers is arrived at, each named as a function of the virus for which it is selective:

| Virus | Oligomer | Length (bases) | Position | Temperature |
|---|---|---|---|---|
| HPV1a | CCTCAGGCGAGAAGCGCGGAC | 21 | 1052 | 72° C. |
| HPV5 | TGTATGGGATCGGGGGCGTTTA | 22 | 1801 | 68° C. |
| HPV6b | CATTAACGCAGGGGCGCCTGAA | 22 | 4761 | 70° C. |
| HPV8 | ACACCGCCGCCAAGACCCCCA | 21 | 3344 | 72° C. |
| HPV11 | GGCGTGTCGGCGCCGCCTAG | 20 | 3416 | 72° C. |
| HPV16 | CAGAACCGGACAGAGCCCAT | 20 | 695 | 64° C. |
| HPV18 | CGGTATCCGCTACTCAGCTTG | 21 | 3448 | 64° C. |
| HPV33 | CGTCCTCCGGTTACTGTAGACA | 22 | 4474 | 68° C. |

Each of the probes proposed above was then compared with each of the HPV sequences by the algorithm of Sellers and Goad, which quotes the "mismatches"[1] and the "gaps"[2]. The results of this treatment show that the probes selected never have more than 75% of homology with the non-homologous sequences. The results obtained are presented in Table I below.

[1] "mismatch": pairing of bases unsuitable for the formation of hydrogen bonds; this pairing hence does not contribute to the stabilization of the hybridized region and will on the other hand frequently have a destabilizing effect. [2] "gap": in the attempt to pair two nucleic acid regions, it may happen that in order to maximise the overall stability of the hybridized region, it is necessary to provide in one of the sequences the existence of one or several unpaired bases; this type of "jump" generally determines a negative contribution to the overall stability of the hybrid.

In each case are retaken: the numbers of pairable bases, "mismatches" and "gaps".

TABLE I

| Target of Probe of | Sequence | | | | | | | |
|---|---|---|---|---|---|---|---|---|
| | HPV1a | HPV5 | HPV6b | HPV8 | HPV11 | HPV16 | HPV18 | HPV33 |
| HPV1a | 21/0/0 | − of 8 | 15/1/2 | 10/0/1 | 13/1/2 | 9/0/1 | − of 8 | 13/1/2 |
| HPV5 | − of 8* | 22/0/0 | − of 8 | 14/1/1 | − of 8 | 12/3/0 | − of 8 | 10/0/1 |
| HPV6b | 11/2/0 | 15/2/1 | 22/0/0 | 12/3/0 | 16/4/0 | 10/0/1 | − of 8 | − of 8 |
| HPV8 | 9/0/1 | 17/4/0 | 9/1/0 | 21/0/0 | 12/1/1 | 9/1/0 | − of 8 | 8/0/0 |
| HPV11 | − of 8 | 11/2/0 | 12/1/0 | 11/1/0 | 22/0/0 | 11/2/0 | 10/1/0 | 10/1/0 |
| HPV16 | 13/1/2 | 12/2/0 | 15/3/1 | 11/2/0 | − of 8 | 20/0/0 | 12/1/1 | − of 8 |
| HPV18 | 10/0/1 | 13/1/2 | 12/2/0 | 10/0/1 | 13/3/0 | 13/3/0 | 21/0/0 | 10/1/0 |
| HPV33 | 10/1/0 | 11/0/2 | 11/2/0 | 12/3/0 | − of 8 | − of 8 | 11/2/0 | 22/0/0 |

*less than 8 pairable bases.

All the situations guarantee highly specific hybridizations, without risk of eroneous signals or troublesome background noise.

EXAMPLE 3

Hybridization of HPV probes with DNA of different virus

The genomes of the HPV6b, 11, 16 and 18 were received cloned in pBR322. When the clones 6b, 11, 16 were digested with BamHI and the clone 18 with EcoRI, the genome of the virus (about 8 kb) of the pBR322 is separated.

(a) Amplification of the clones

The presence of HPV genomes in the clones was confirmed by restriction. The clones were then amplified and the DNA was purified on a cesium chloride gradient.

(b) Separation of the DNA of the HPV viruses on agarose gel

2 μg of each DNA were digested either with BamHI for the clones 6b, 11 and 16, or with EcoRI for the clone 18. The 2 μg of each DNA were redistributed adjacently and in parallel on four 0.8% agarose gels (500 ng DNA/clone/gel) close to a radioactively labelled size label (lambda HindIII-EcoRI). After 3 hours of migration at 80 Volts in TBE1X (Tris 90 mM, EDTA 2.5 mM, boric acid 90 mM, pH8), the gels were denatured (NaOH, 0.5 M, NaCl 0.5 M) for 30 minutes, rinsed with water then neutralized (NaCl 1.5 M, Tris HCl pH 8, 0,5 M) for 30 minutes at room temperature. The gels were then deposited on a Whatman 3 MM paper, covered with saranwrap and placed to dry under vacuum for 1 hour at room temperature and 1 hour at 60° C.

(c) Labelling with $^{32}p$ of specific HPV probes

Synthetic oligomers characteristic of HPV6b, 11, 16 and 18 were synthetized.

| | | Size | Temperature |
|---|---|---|---|
| HPV6b | CATTAACGCAGGGGCGCCTGAA | 22 mer | 70° C. |
| HPV11 | GGCGTGTCGGCGCCGCCTAG | 20 mer | 72° C. |
| HPV16 | CAGAACCGGACAGAGCCCAT | 20 mer | 64° C. |
| HPV18 | CGGTATCCGCTACTCAGCTT | 20 mer | 60° C. |

These sequences are complementary with the non-coding string of the HPVs.

The four oligomers were labelled with $^{32}p$ by kination according to the following procedure: 1 μg of each oligomer was mixed, in a final volume of 30 μl, with 30 uCi of gamma $^{32}$P ATP (3,000 Ci/mmole), 5 units of T4 polynucleotide kinase, 67 mM Tris HCl pH 8, 10 mM MgCl$_2$, 10 mM dithiothreitol and incubated 45 minutes at 37° C., The labelled oligomers were separated from the free nucleotides by chromatography on Sephadex G50. The specific activity obtained amounted to 65.10$^6$ cpm/μg of oligomer engaged in the reaction.

(d) Hybridization on gel with labelled probes

The agarose gels were detached from the Whatman paper by dipping them for some minutes in water. Each gel was hybridized with one of the four radioactively labelled oligomers, in a volume of 5 ml of hybridization mixture comprising 2.10$^6$ cpm/ml of radioactive oligomers, 0.1% SDS, 100 μg/ml of salmon sperm DNA denatured 10 minutes at 100° C., 5×SSPE (NaCl 0.9 M, NaH$_2$PO$_4$, EDTA pH 8, 5 mM). The incubation was carried out in sealed plastic bags and in a bath stirred at 60° C. for 14 hours.

(e) Washing and exposure

The gels were washed twice for 15 minutes, then for 1 hour at ambiant temperature, 10 minutes at 60° C. and finally 1 hour at ambiant temperature in 6XSSC (0.9 M NaCl, 90 mM trisodium citrate, pH 7). After having been deposited on a sheet of Whatman paper and covered with saranwrap, the gels were placed exposed between two reinforcing screens at −70° C. for 14 hours (Film Kodak X-OmatS).

(f) Results

Four duplicates of a gel containing DNA of HPV6b clones 11, 16 and 18 were each hybridized with one of the four oligomers. It was seen that on the gel A only HPV6b is recognized by the probe 6b; on the gel B, only HPV11 is recognized by the probe 11; on the gel C, only HPV16 is recognized by the probe 16 and lastly on the gel D, only HPV18 is recognized by the probe 18.

Figure 1:
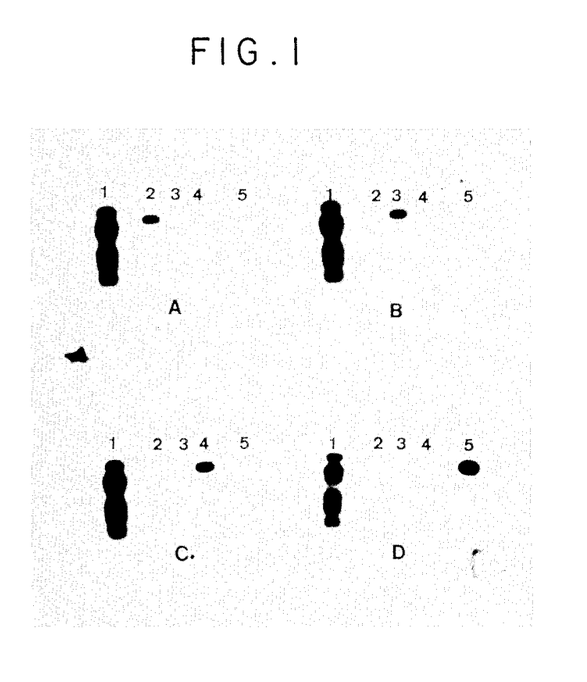
FIG. 1 represents a gel corresponding to the selective hybridization of the HPV synthetic probes according to the invention with the DNAs of the HPV viruses.

It is seen that each probe recognizes the corresponding HPV exclusively to the exclusion of the other HPV types (FIG. 1).

Hybridization of HPV probes on human genomic DNA

Figure 2:
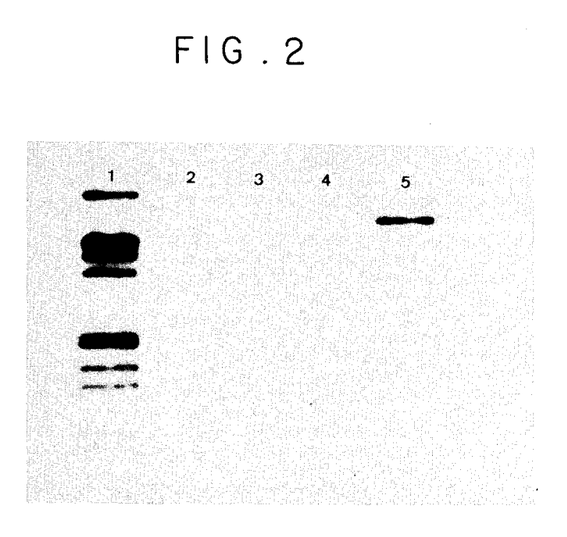
FIG. 2 represents a gel corresponding to the hybridization of the genome DNA with specific HPV probes according to the invention:
1. lambda EcoRI-HindIII - radioactive standards of size,
2. none,
3. human genome DNA (10 ug) digested with EcoRI,
4. none,
5. DNA of the HPV virus (6b, 11, 16 or 18) hybridized with HPV specific probe (6b, 11, 16 or 18)

In addition, there were deposited on 4 gels, 4×10 μg of genomic DNA isolated from lymphocytes, digested with EcoRI, and 200 ng of DNA of one of the 4 HPV clones. Each gel was hybridized with the probe corresponding to the HPV type present on the gel (positive control) and washed as described previously. After 70 hours exposure, absolutely no trace of a specific hybridization of the four types of probes tested on the human genomic DNA was detected (FIG. 2).

EXAMPLE 4

Hybridization of HPV clones with probes common to all the known HPV types (a) Preparation of the gels The clones of the HPVs 6b, 11, 16 and 18 were digested with BamHI or EcoRI. 600 ng of each clone was distributed in parallel over four gels and in adjacence with the other clones, and close to the radioactive size label, the lambda HindIII-EcoRI (150 ng DNA/clone/gel). After 3 hours migration at 80 Volts, the gels were denatured, neutralized and dried under vacuum.

(b) Kination of common probes (labelling with $^{32}$P)

The longest sequence common to all the virus types whose sequence was known, was determined with the computer. This common sequence was a fragment of 12 bases. This fragment being too short, the probes were extended by 6 bases (7 bases for the probe 8) upstream, and by 6 bases downstream from this fragment. The sequences were as follows:

| Probe | | Size | Temperature |
|---|---|---|---|
| HPV1a | ATGCTTTAAAACGAAAGTTACTTT | 24 | 60° C. |
| HPV6b HPV11 | AGGACCTAAAACGAAAGTATTTAG | 24 | 64° C. |
| HPV8 HPV5 | CAAAAACTAAAACGAAAGTATCTTA | 25 | 62° C. |
| HPV16 | AGGTTCTAAAACGAAAGTATTTGG | 24 | 64° C. |
| HPV18 | ATGTTTTAAAACGAAAGTTTGCAG | 24 | 62° C. |
| HPV33 | GTGCACTAAAACGAAAGTTTGCCG | 24 | 70° C. |

These probes were complementary with the coding string. As the probes 6b and 11 were perfectly identical, only one of the two was synthetized (probe 6b/11). These probes were labelled with $^{32}$P by kination as previously described.

(c) Hybridization of the gels

Each gel was hybridized with a batch of probe, in a volume of 5 ml of hybridization mixture containing 0.1% SDS, 100 μg/m 1 of DNA of denatured salmon sperm, 5×SSPE in a sealed plastic bag, at 60° C. for 15 hours.

The hybridization mixture A contained 10$^6$ cpm/ml of each of the probes (1a, 6b/11, 8/5, 16, 18 and 33).

Mixture B contained 10$^6$ cpm/ml of each of the probes with the exception of the probe 6b/11.

Mixture C contained 10$^6$ cpm/ml of each of the probes with the exception of probe 16.

Mixture D contained 10$^6$ cpm/ml of each of the probes with the exception of the probe 18.

(d) Washing and exposure

The four gels were washed in 6XSSC for one hour at room temperature, 10 minutes at 60° C., then again one hour at room temperature. The gels were exposed between two reinforcing screens for two hours at −80° C.

Figure 3:
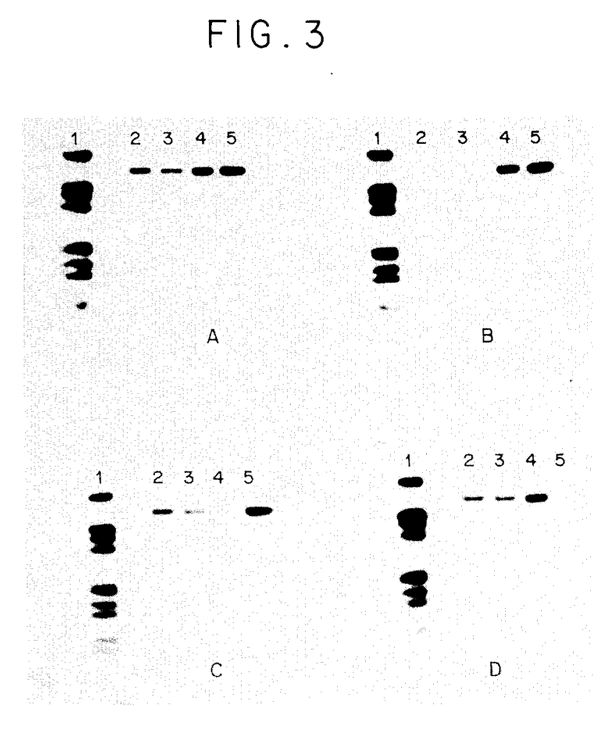
FIG. 3 represents a gel corresponding to the hybridization of the HPV clones with probes common to all the virus types.

(e) Results (FIG. 3)

Hybridization of the HPV clones with the probes common to all the virus types.
1. lambda HindIII-EcoRI,
2. HPV6b BamHI,
3. HPV11 BamHI,
4. HPV16 BamHI,
5. HPV18 EcoRI A. Hybridization with all of the probes (1a, 6b/11, 16, 18, 33),
B. Hybridization with all of the probes with the exception of probe 6b/11,
C. Hybridization with all of the probes with the exception of probe 16,
D. Hybridization with all of the probes with the exception of probe 18.

These results show clearly that the common probes are hybridized with all of the clones in the experiment and that the experimental conditions even permit differentiation between the clones by the specificity of the extension ends of the common sequence.

EXAMPLE 5

Hybridization of the HPV specific probes with the DNA of the different viruses (Second and third series of probes)

The genomes of HPV6b, 11, 16 and 128 were received cloned in pBR322. When the clones 6b, 11, 16 were digested with BamHI and the clone 18 with EcoRI, the genome of the virus (about 8 kb) was separated from the pBR322.

(a) Amplification of the clones

The presence of the HPV genomes in the clones was confirmed by restriction. The clones were then amplified and the DNA was purified on a cesium chloride gradient.

(b) Separation of the DNA of HPV viruses on agarose gel 1.6 μg of each DNA was digested either with BamHI for the clones 6b, 11 and 16, or with EcoRI for the clone 18. The 1.6 μg of each DNA was distributed adjacently and in parallel over eight agarose gels 0.8% (200 ng DNA/clone/gel) close to a radioactively labelled size label (lambda HindIII-EcoRI). After 3 hours of migration at 80 Volts in TBE 1X (Tris 90 mM, EDTA 2.5 mM, boric acid 90 mM, pH 8), the gels were denatured (NaOH 0.5 M, NaCl 1.5 M) for 30 minutes, rinsed with water, then neutralized (NaCl 1.5 M, Tris HCl pH 8, 0.5 M) for 30 minutes at room temperature. The gels were then deposited on Whatman 3MM paper, covered with saranwrap and placed to dry under vacuum for 1 hour at room temperature and 1 hour at 60° C.

(c) Labelling with $^{32}P$ of the specific HPV probes

The synthetic oligomers characteristic of HPV6b, 11, 16 and 18 were synthetized. This is the second series of specific probes:

| Virus | Oligomer | Length | Position | Gene | Temp. |
|---|---|---|---|---|---|
| HPV6b | CGCCCCTGCGTTAATGATTGCC | 22 | 4776–4755 | L2 | 70° C. |
| HPV11 | AATAGCAGGCTTGGGAGAGCTTC | 23 | 4659–4637 | L2 | 70° C. |
| HPV16 | CAGTAGAGATCAGTTGTCTCTGGT | 24 | 632–609 | E7 | 70° C. |
| HPV18 | GGGCCGTGGGTGATACAATGGG | 22 | 5507–5486 | L2 | 72° C. |

In addition, a third series of probes each specific with one type of human papilloma virus, but situated in the region E7 of the genome of each of these viruses, was synthetized in parallel.

E7 probe series:

| Virus | Oligomer | Length | Position | Gene | Temp. |
|---|---|---|---|---|---|
| HPV6b | GAATCTTGTCCGTCCACTTCGTC | 23 | 663–641 | E7 | 70° C. |
| HPV11 | GTTTGTCCACCTTGTCCACCTCA | 23 | 656–634 | E7 | 70° C. |
| HPV16 | CAACCGAAGCGTAGAGTCACACT | 23 | 762–740 | E7 | 70° C. |
| HPV18 | CTCAATTCTGGCTTCACACTTACAA | 25 | 808–784 | E7 | 70° C. |

In these two series, the probes correspond to the reverse string of HPVs, the positions indicated are marked on the direct string.

The eight oligomers were labelled with the $^{32}P$ by kination according to the following procedure: 0.1 μg of each oligomer was mixed, in a final volume of 30 μl, with 30 uCi of gamma $^{32}P$ ATP (3,000 Ci/mmole), 5 units T4 polynucleotide kinase, 67 mM Tris HCl pH 8, 10 mM MgCl$_2$, 10 mM dithiothretiol and incubated 45 minutes at 37° C. The labelled oligomers were separated from the free nucleotides by chromatography on Sephadex C50. The specific activity obtained amounts to $5.10^8$ cpm/μg of oligomer engaged in the reaction.

(d) Hybridization on gel with labelled probes

The agarose gels were detached from the Whatman paper by dipping them for some minutes in water. Each gel was hybridized with one of the four radioactively labelled oligomers, in a volume of 5 ml of hybridization mixture comprising $2.10^6$ cpm/ml of reactive oligomers, 0.1% SDS, 100 μg/m of DNA of salmon sperm denatured 10 minutes at 100° C., 5×SSPE (NaCl 0.9 M, NaH$_2$PO$_4$ 50 mM, EDTA pH 8, 5 mM). Incubation was performed in sealed plastic bags and in a bath stirred at 65° C. for about 14 hours.

(e) Washing and exposure

The gels were washed twice 15 minutes, then 1 hour at room temperature, 10 minutes at 65° C. and lastly 1 hour at room temperature in 6XSSC (0.9 M NaCl, 90 mM trisodium citrate, pH 7). After being deposited on a sheet of Whatman paper and covered with saranwrap, the gels were put under exposure between two reinforcing screens at −70° C. from 2 to 14 hours (Film Kodak X-OmatS).

(f) Results

Figure 4:
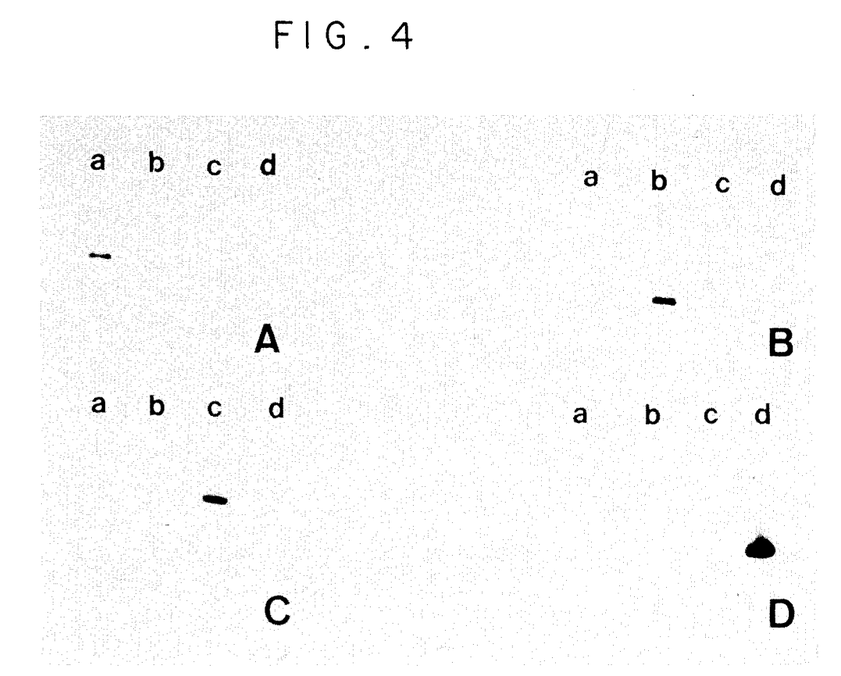
FIG. 4 shows the selective hybridization of the HPV synthetic specific probes with DNAs of the HPV virus.
 a: DNA of the HPV6b virus, digested with BamHI
 b: DNA of the HPV11 virus, digested with BamHI
 c: DNA of the HPV16 virus, digested with BamHI
 d: DNA of the HPV18 virus, digested with EcoRI
 A: specific probe of HPV6b
 B: specific probe of HPV11
 C: specific probe of HPV16
 D: specific probe of HPV18
Figure 5:
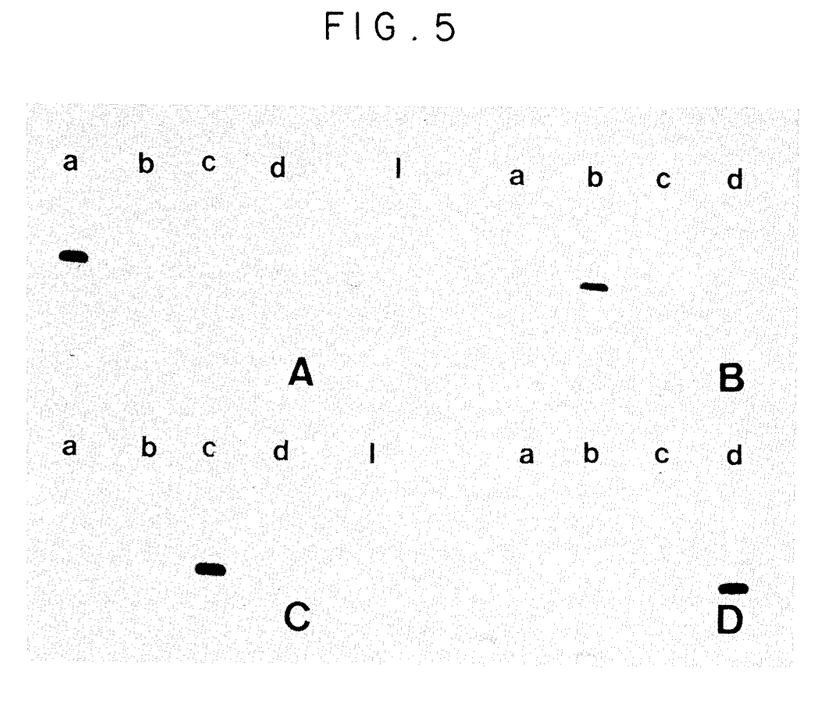
FIG. 5 shows the selective hybridization of synthetic probes directed against the E7 region of the HPV genome with DNAs of the HPV virus.
 a: DNA of the HPV6b virus, digested with BamHI
 b: DNA of the HPV11 virus, digested with BamHI
 c: DNA of the HPV16 virus, digested with BamHI
 d: DNA of the HPV18 virus, digested with EcoRI
 A: specific probe of HPV6b
 B: specific probe of HPV11
 C: specific probe of HPV16
 D: specific probe of HPV18
 1: radioactive DNA fragments lambda EcoRI-HindIII - size standards.

Two series of four duplicates containing DNA of clones HPV6b, 11, 16 and 18 were each hybridized with one of the four oligomers of the two specific probe series. It is seen that HPV6b is only recognized by probes 6b (FIG. 4A and 5A), that HPV11 is only recognized by probes 11 (FIG. 4B and 5B), that HPV16 is only recognized by probe 16 (FIG. 4C and 5C) and lastly that only HPV18 is recognized by probes 18 (FIG. 4D and 5D). Each probe recognized the corresponding HPV exclusively to the exclusion of the other types of HPV.

EXAMPLE 6

In order to increase the sensitivity of the detection of infections by HPVs, the technique of enzymatic amplification of the DNA currently called PCR (polychain reaction) in the scientific literature of the speciality was applied to the amplification of the DNAs of the HPVs.

This step was aimed at increasing the sensitivity whilst preserving the specificity of the detection illustrated above in this specification. The region of viral genomes selected for the amplification comprised consequently the target segment of probes of the E7 gene. The specificity of the amplification is ensured by the definition of sequences initiated of the polymerization by a thermostable polymerase on each side of the target sequence of the probes. The sequences of each of the pairs of primers were hence selected so as to amplify specifically the fragment of the gene of the virus to which they were addressed, with the exclusion of all the others. In addition, the relative position of each of the primers with respect to its pair was selected so as to amplify fragments of a different size for each viral DNA and to permit rapid and direct identification of the type or of the types of human papilloma virus by separation of the amplified fragments according to their length, on an electrophoresis gel. An additional criterion of the choice of sequences of primers takes into account their composition and their length which must permit specific hybridization with the complementary sequence of the DNA to be amplified, at optimal operating temperatures of the thermostable polymerases.

The following sequences, intended to serve as oligomeric primers for the enzymatic amplification reactions were defined taking into account the above-mentioned criteria.

|  | position | Length of amplified fragment |
|---|---|---|
| for HPV1a |  |  |
| GTTGCTTCCTGTGCCTATTGCG | 673–694 | 90 |
| CAGAAGGAGTTCCTCCAGCTG | 762–742 |  |
| for HPV5 |  |  |
| ATTATTCTGGAGCTCAGTGAGGT | 693–715 | 252 |
| ACAGTCAGGGCACAGGAGCTGC | 944–922 |  |
| for HPV6B |  |  |
| TGTATTAGACCTGCAACCTCCAG | 562–584 | 224 |
| TTCCCAACAGAAGCTGTTGCAC | 785–764 |  |
| for HPV8 |  |  |
| CTAGACATCGAAAGAACTGTATTC | 779–802 | 156 |
| GCACTCAGGACACAGAAGCTGT | 934–913 |  |
| for HPV11 |  |  |
| AGTACTAGACCTGCAGCCTCCT | 562–583 | 206 |
| GTAGTTGTCTGATGTCTCCGTC | 767–746 |  |
| for HPV16 |  |  |
| GCAGAACCGGACAGAGCCCA | 694–713 | 127 |
| GTGTGCCCATTAACAGGTCTTCC | 798–820 |  |
| for HPV18 |  |  |
| GCCCGACGAGCCGAACCACA | 740–759 | 109 |
| GGAATGCTCGAAGGTCGTCTG | 848–828 |  |
| for HPV33 |  |  |
| GGCTTGGACCGGCCAGATGG | 681–700 | 178 |
| GTGCACAGGTAGGGCACACAA | 858–838 |  |

Identical experiments also attest to the specificity of the other probes according to the invention and particularly of the specific probes of the virus sub-groups according to the invention.

We claim:

1. Nucleic acid probe useful for detecting indifferently eight types of human papilloma virus, HPV1a, HPV5, HPV6b HPV8, HPV11, HPV16, HPV18 and HPV33, consisting of a sequence of labelled nucleic acids, said probe consisting essentially of a mixture of oligomers, which include a sequence of 12 nucleotides X-A-A-A-A-C-G-A-A-A-A-G-X with X=T or U, or its complement extended on each side by 1 to 10 corresponding nucleotides for each of the eight virus types.

2. Nucleic acid probe common to the eight different types of HPV virus, HPV1a, HPV5, HPV6b, HPV8, HPV11, HPV16, HPV18 and HPV33, said probe consisting essentially of a mixture of six oligomers, which include a common sequence of twelve nucleotides X-A-A-A-A-C-G-A-A-A-G-X and with X=T or U, or its complement extended on each side by 1 to 10 corresponding nucleotides for each of the eight virus types.

3. Probe according to claim 2, wherein the mixture of the six oligomers are:
for HPV1a A-X-G-C-X-X-X-A-A-A-A-A-C-G-A-A-A-G-X-X-A-C-X-X-X
for HPV6b and HPV11 A-G-G-A-C-C-X-A-A-A-A-A-C-G-A-A-A-G-X-A-X-X-X-A-G
for HPV8 and HPV5 C-A-A-A-A-A-C-X-A-A-A-A-C-G-A-A-A-G-X-A-X-C-X-X-A
for HPV16 A-G-G-X-X-C-X-A-A-A-A-C-G-A-A-A-G-X-A-X-X-X-G-G
for HPV18 A-X-G-X-X-X-X-A-A-A-A-C-G-A-A-A-G-X-X-X-G-C-A-G
for HPV33 G-X-G-C-A-C-X-A-A-A-A-C-G-A-A-A-G-X-X-X-G-C-C-G
with X=T or U or their complements.

4. Specific probe of nucleic acids for the detection of the HPV1a type of human papilloma virus, said probe consisting essentially of an oligomer selected from among:
CCXCAGGCGAGAAGCGCGGAC
CXGXCCCXXCXGCGCGAGACGX
XGXCCCXXCXGCGCGAGACGXXGGAAGX-AXACACA
GACCGXCCXCGCGGAXCACAG
GACCGXCCXCGCGGAXCACAGCGCCAXX-AGACAGC
with X=T or U and their complements.

5. Specific nucleic acid probe for the detection of the HPV5 type of human papilloma virus, said probe consisting essentially of an oligomer selected from among:
XGXAXGGGAXCGGGGGCGXXXA
XXGXAXGGGAXCGGGGGCGXXXA
XGXAXGGGAXCGGGGGCGXXXAGCCAXG-GACCAXA
GCCXGACAACGAAAGGAXCXCXXA
GAGGAGCCXGACAACGAAAGGAXCXCXX-ACAAAGX
with X=T or U and their complements.

6. Specific probe of nucleic acids for the detection of the HPV6b type of human papilloma virus, said probe consisting essentially of an oligomer selected from among:
CAXXAACGCAGGGGCGCCXGAA
GGCAAXCAXXAACGCAGGGGCG
GCAAXCAXXAACGCAGGGGCGCCX-GAAAXXGXGCC
GACGAAGXGGACGGACAAGAXXC
GAGGXGGACGAAGXGGACGGACAAGAXX-CACAACC
with X=T or U and their complements.

7. Specific probe of nucleic acids for the detection of the HPV8 type of human papilloma virus, said probe consisting essentially of an oligomer selected from among:
ACACCGCCGCCAAGACCCCCA
GCAGCXCAGXCCGCGGCXCC
GCAGCXCAGXCCGCGGCXCCAGXCAAXAX-CACXGX
XGXCAACGCAACXGAXXCGGGXAX
CXXXXXGXCAACGCAACXGAXXCGGGXAX-CAGGAC
with X=T or U and their complements.

8. Specific probe of nucleic acids for the detection of the HPV11 type of human papilloma virus, said probe consisting essentially of an oligomer selected from among:
GGCGXGXCGGCGCCGCCXAG
GAAGCXCXCCCAAGCCXGCXAXX
XAXAXACCCXXGGGAAGCXCX-CCCAAGCCXGCXAX
XGAGGXGGACAAGGXGGACAAAC
AGAAGAXGAGGXGGACAAGGX-GGACAAACAAGACG
with X=T or U and their complements.

9. Specific probe of nucleic acids for the detection of the HPV16 type of human papilloma virus, said probe consisting essentially of an oligomer selected from among:
CAGAACCGGACAGAGCCCAX
ACCAGAGACAACXGAXCXCXACXGX
and ACAAGCAGAACCGGACAGAGCCCA
XGXXAGAXXXGCAACCAGAGACAACX-GAXCXCXAC
AGXGXGACXCXACGCXXCGGXXG
XXGCAAGXGXGACXCX-ACGCXXCGGXXGXGCGXAC
with X=T or U and their complements.

10. Specific probe of nucleic acids for the detection of the HPV18 type of human papilloma virus, said probe consisting essentially of an oligomer selected from among:
CGGXAXCCGCXACXCAGCXXG
CCCAXXGXAXCACCCACGGCCC
CCCAXXGXAXCACCCACGGCCCCXGCCXCX-ACACA
XXGXAAGXGXGAAGCCAGAAXXGAG
AXGXGXXGXAAGXGXGAAGCCAGAAXX-GAGCXAGX
with X=T or U and their complements.

11. Specific probe of nucleic acids for the detection of the HPV33 type of human papilloma virus, said probe consisting essentially of an oligomer selected from among:
CGXCCXCCGGXXACXGXAGAXA
GXCCXCCGGXXACXGXAGACACX
XCCXCCGGXXACXGXAGACACXGX-XGGACCXXXAG
AGCAAGXGACCXACGAACCAXACA
AGXACAGCAAGXGACCXACGAACCAX-ACAGCAACX
with X=T or U and their complements.

12. Specific probe of nucleic acids of the subgroup of HPV virus constituted by HPV16, HPV18 and HPV33, said probe consisting essentially of the oligomer
XXAGGCACAXAXXXX
with X=T or U or its complement.

13. Specific probe of nucleic acids of the subgroup of HPV virus constituted by HPV16 and HPV 18, said probe consisting essentially of the oligomer
AXAXCAAAXAXXAGXGAAGX
with X=T or U or its complement.

14. Specific probe of nucleic acids of the subgroup of HPV virus constituted by HPV5 and HPV8, said probe consisting essentially of the oligomer
CAAACAACAGXXGCXGACAAXAXXXX-AAAAXAXGGCAGXGCXGGXGXAXXX XXXGG
with X=T or U or its complement or a fragment of the latter comprising between 18 and 35 oligomers such as
XAXGGCAGXGCXGGXGXAXXXXXXG
with X=T or U or its complement.

15. Probe of nucleic acids according to claim 1, said probe being labelled by one of the methods known for the labelling of DNA or RNA probes, selected particularly from among radioactive labelling, such as 32p and enzymatic labelling, such as with biotin.

16. Method for detecting a type of HPV virus or of a sub-group of HPV virus by means of a probe, according to claim 1, said method comprising hybridizing said probe with a DNA or RNA sequence of said HPV virus, as the case may be, previously denaturated if it was initially double-stranded.

17. Method of detection according to claim 16, consisting essentially of using the PCR method of amplification with following oligomeric primers:

| | position | length of amplified fragment |
|---|---|---|
| for HPV1a | | |
| GTTGCTTCCTGTGCCTATTGCG | 673–694 | 90 |
| CAGAAGGAGTTCCTCCAGCTG | 762–742 | |
| for HPV5 | | |
| ATTATTCTGGAGCTCAGTGAGGT | 693–715 | 252 |
| ACAGTCAGGGCACAGGAGCTGC | 944–922 | |
| for HPV6B | | |
| TGTATTAGACCTGCAACCTCCAG | 562–584 | 224 |
| TTCCCAACAGAAGCTGTTGCAC | 785–764 | |
| for HPV8 | | |
| CTAGACATCGAAAGAACTGTATTC | 779–802 | 156 |
| GCACTCAGGACACAGAAGCTGT | 934–913 | |
| for HPV33 | | |
| GGCTTGGACCGGCCAGATGG | 681–700 | 178 |
| GTGCACAGGTAGGGCACACAA | 858–838 | |

* * * * *